(12) United States Patent
de Groot

(10) Patent No.: US 9,408,354 B2
(45) Date of Patent: Aug. 9, 2016

(54) WATERMELON VARIETY NUN 01009 WMW

(71) Applicant: Nunhems B.V., Nunhem (NL)

(72) Inventor: Erik de Groot, Nonantola (IT)

(73) Assignee: Nunhems B.V., Nunhem (NL)

( * ) Notice: Subject to any disclaimer, the term of this patent is extended or adjusted under 35 U.S.C. 154(b) by 710 days.

(21) Appl. No.: 13/762,564

(22) Filed: Feb. 8, 2013

(65) Prior Publication Data

US 2013/0180017 A1    Jul. 11, 2013

(51) Int. Cl.
  *A01H 5/08* (2006.01)
  *A01H 5/10* (2006.01)
  *A01H 5/00* (2006.01)
  *A01H 1/02* (2006.01)
  *A01H 4/00* (2006.01)
  *C12N 15/82* (2006.01)

(52) U.S. Cl.
  CPC .. *A01H 5/08* (2013.01); *A01H 1/02* (2013.01); *C12N 15/8261* (2013.01); *A01H 4/00* (2013.01)

(58) Field of Classification Search
  None
  See application file for complete search history.

(56) References Cited

U.S. PATENT DOCUMENTS

2013/0180017 A1 * 7/2013 de Groot ............ C12N 15/8261 800/308

OTHER PUBLICATIONS

Boyhan et al (2003 Watermelon and Cantaloupe Variety Trials).*

* cited by examiner

*Primary Examiner* — Lee A Visone

(57) ABSTRACT

The present invention relates to plants and plant parts of a watermelon variety NUN 01009 WMW, seeds from which the plant can be grown and seedless fruit produced on the plant, as well as vegetative reproductions of NUN 01009. Further, the invention relates to natural or induced phenotypic variants of the plant, such as mutants or somaclonal variants.

12 Claims, No Drawings

WATERMELON VARIETY NUN 01009 WMW

FIELD OF THE INVENTION

The present invention relates to the field of plant breeding. In particular, the invention provides for a new and distinct variety of watermelon designated NUN 01009 WMW (or "NUN 01009" or "NUN1009") and parts thereof and seeds from which the variety can be grown. The invention further relates to vegetative reproductions of NUN 01009, methods for in vitro tissue culture of NUN 01009 explants and also to phenotypic variants of NUN 01009 WMW. The invention further relates to methods of producing triploid, seedless watermelon fruits of NUN 01009 or of phenotypic variants of NUN 01009 WMW.

Seedless watermelon (*Citrullus lanatus* (Thunb.) Matsum. and Nak.) are produced by using pollen from diploid male parent plants to fertilize flowers of tetraploid maternal parent plants. Pollination of the tetraploid flowers with diploid pollen leads to hybrid F1 seeds which are triploid (Kihara, 1951, Proceedings of American Society for Horticultural Science 58: 217-230; Eigsti 1971, Hort Science 6: 1-2). The triploid hybrid plants grown from these F1 seeds are self-infertile as they produce sterile pollen due to chromosome imbalance (Fehr, 1987). The triploid hybrids, therefore, need to be pollinated by a diploid pollenizer to produce watermelon fruit. Triploid plants are, therefore, interplanted with pollenizer plants for fruit production. The "seedless" fruit produced after pollination on the triploid hybrid plant are not truly seedless, but often contain some undeveloped, small, pale seeds, which are edible.

For optimal fruit set, sufficient viable pollen is required. Plants are generally planted at a ratio of 1 pollenizer per every 2-4 triploid plants. Triploid plants and pollenizers are either planted in separate rows (e.g. 1 row of pollenizer and 2-4 rows of triploids), or interplanted within rows (e.g. planting 1 pollenizer plant in between 2 to 3 triploid plants in the same row), or interplanted in narrow rows between rows of triploids (see US 2006/0168701 Table 2). The fruit produced on the pollenizer plants preferably has a different rind pattern from the fruit on the triploid hybrids, so that these can be easily distinguished.

Although hybrid triploid (seedless) watermelons have been grown in the United States for over 40 years, there is still a need for improved varieties. Consumer demand is high, and the seedless fruit of triploid watermelons are very desired, both for the fresh and the processed market. Many different triploid watermelon varieties exist (see e.g. cuke.hort.ncsu.edu/cucurbit/wmelon/wmcultab.html), producing fruits of different sizes and shapes, as well as different fruit quality. Grading of fruits is usually done by fruit weight, to distinguish "mini" watermelons, with weights of less than 6 pounds (2.72 kg), "icebox" watermelons with weights of 8-12 pounds (3.62 kg-5.44 kg) or, according to others, of 6 to 15 pounds (2.72 kg to 6.8 kg) and "picnic" watermelons of above the icebox size, so either above 12 lbs (above 5.44 kg) or above 15 pounds (above 6.8 kg).

A new variety of triploid watermelon is provided herein (designated NUN 01009), as are seeds from which the new variety can be grown. Also phenotypic variants of the new variety are an embodiment of the invention, as are cells, tissues, plant parts, fruits of the new variety and of the phenotypic variants thereof. The marketable, fruits are "icebox" size, having an average fruit weight of 6.1 kg (13.44 lbs), which is significantly larger than the average fruit size of the most similar triploid variety Millionaire (Harris Moran), which has an average fruit weight of 5.3 kg (11.68 lbs).

Further, a method for growing the new variety or the phenotypic variant of the variety and for producing seedless fruits is provided herein.

SUMMARY OF THE INVENTION

The invention provides for a new triploid watermelon variety designated NUN 01009 representative seed of said variety having been deposited under Accession Number NCIMB 42569, and plant parts of the new variety such as (harvested) fruits, or parts of the fruits.

Non-limiting examples for parts of said plant are flower, fruit, stalk, leaf, shoot, shoot tip, seed or parts of the seed, mature or immature embryo, embryo sac, cutting, scion, root, root-stock, root tip, pistil, anther, cotyledon, hypocotyl, meristematic cell, stem, cell, in vitro cell cultures or tissue cultures, callus, protoplast, meristem, petiole, bud or parts of any of these such as parts of fruits. In some embodiments, parts of a watermelon plant designated NUN 01009 are provided which are suitable for vegetative reproduction, and a tissue culture or cell culture of a watermelon plant designated NUN 01009 is provided.

The in vitro tissue culture or cell culture comprises or consists of tissues or cells of NUN 01009 which can be regenerated into a whole plant, to produce a clonal (vegetative) reproduction of NUN 01009, or of a phenotypic variant of NUN01009, which differs from NUN 01009 in one or more morphological and/or physiological characteristics when grown under the same conditions. Preferably, the phenotypic variant retains however the distinguishing characteristics of NUN 01009, especially the distinguishing characteristics numbered 1) to 5), but optionally also one or more, or all, of the distinguishing characteristics numbered 6) to 12) (vide infra).

The invention also provides for seeds of the new variety (i.e. seeds from which the new variety can be grown), representative seed of said variety having been deposited under Accession Number NCIMB 42569, a plant, or a part thereof (such as a fruit), produced by growing said seed.

In a further aspect, the invention provides a vegetative reproduction (clonal reproduction) of NUN 01009. Also provided are explants of NUN 01009 and in vitro cell or tissue cultures of NUN 01009, which comprise cells or tissues that can be regenerated into a seedling and plant that has all the morphological and physiological characteristics of NUN 01009 when grown under the same conditions.

In a further aspect, the invention provides a vegetative reproduction (clonal reproduction) derived from NUN 01009, which is, however a phenotypic variant of NUN 01009. Also provided are explants of NUN 01009 and in vitro cell or tissue cultures of NUN 01009, which comprise cells or tissues that can be regenerated into a seedling and plant that does not have all the morphological and physiological characteristics of NUN 01009 when grown under the same conditions, i.e. the vegetative reproduction is a phenotypic variant of NUN 01009. The phenotypic variant of NUN 01009 may be a somaclonal variant, a mutant or an off-type. However, the variant phenotype is preferably genetically stable also in the mature plants regenerated from the cell or tissue culture. That means, the phenotypic variant does not show variation in phenotype which are transient and are not genetically stable.

Also provided is a method of producing triploid, seedless watermelon fruits of NUN 01009 or of a phenotypic variant of NUN 01009, said method comprising:
(a) interplanting diploid pollenizer plants and triploid hybrid plants according to the invention in one field, (b) allowing pollination of flowers of the triploid hybrid plants with pollen of the diploid pollenizer plants, and optionally allowing pollination of flowers of the diploid pollenizer plants with pollen of the diploid pollenizer plants, (c) harvesting fruits produced on the triploid hybrid plants and, optionally, harvesting fruits produced on the diploid pollenizer plants.

Moreover, also a phenotypic variant of (or derived from) a watermelon plant designated NUN 01009 is provided, e.g., an phenotypic variant of NUN 01009 having one or two or three physiological and/or morphological characteristics which are different from those of NUN 01009 and which otherwise has essentially all physiological and morphological characteristics when grown under the same environmental conditions of a watermelon plant designated NUN 01009. In one aspect the phenotypic variant of NUN 01009 differs from NUN 01009 in one or more characteristics, which are not the distinguishing characteristics 1) to 5). In other words, in one embodiment the phenotypic variant of NUN 01009 differs from NUN 01009 in one, two, three or more morphological and/or physiological characteristics, but does not differ from NUN 01009 in the distinguishing characteristics 1) to 5), and optionally does further not differ from NUN 01009 in one, two, three, four, five or all six distinguishing characteristics 6) to 12).

Such a phenotypic variant is obtainable by selecting a natural or induced mutant, or a somaclonal variant from cells, or tissues, or plant parts, or from a plurality of plants, of NUN 01009, or from seeds or seed parts of NUN 01009, a representative sample of which has been deposited under NCIMB 42569.

In another aspect the invention refers to packages, e.g., a container, a bag and the like, comprising at least one of the following: seeds or seed pellets of watermelon variety designated NUN 01009, watermelon seedlings or plant(s) designated NUN 01009 or a phenotypic variant of NUN 01009, and parts of watermelon plant(s) designated NUN 01009 or parts of a phenotypic variant of NUN 01009. In one aspect the parts are triploid, seedless fruits harvested from NUN 01009 plants or from phenotypic variants of NUN 01009, preferably marketable fruits.

Also provided is a food or feed product comprising at least a part of a watermelon plant designated NUN 01009 or of an phenotypic variant of NUN 01009, such as a fruit or fruit part produced on the plant designated NUN01009 or on the phenotypic variant of NUN01009 after pollination with diploid pollen of another watermelon plant.

In another aspect the invention provides a method of producing a seedless, triploid watermelon fruit comprising pollinating the flowers of a first parent watermelon plant designated NUN01009 or a phenotypic variant of NUN01009 with pollen of a second watermelon plant and harvesting the resultant seedless fruit NUN 01009 or from the phenotypic variant of NUN 01009.

Also provided are seedless fruit obtained by said method.

In a further aspect the invention provides a method for vegetative reproduction of NUN 01009, said method comprises the steps of:
a) Providing an explant of NUN 01009,
b) Culturing said explant in an in vitro culture,
c) Providing a shooting and rooting medium to said explants,
d) Allowing rooted plants to grow.

In another aspect the invention provides a method for identifying and/or selecting a phenotypic variant of NUN 01009, said method comprises the steps of:
a) Providing an explant of NUN 01009,
b) Culturing said explant in an in vitro culture,
c) Providing a shooting and rooting medium to said explants,
d) Allowing rooted plants to grow,
e) Identifying and/or selecting a phenotypic variant.

Explants may be any plant parts of NUN 01009 which is regenerable into a whole plant, such as parts of cotyledons, shoot tips, embryos, hypocotyls, leaves, stalk, cells, protoplasts, callus, meristems, etc.

Optionally, the explants may be treated with a mutagen, such as X-rays, UV-radiation, EMS or another chemical mutagen.

In another aspect the invention provides a method for identifying and/or selecting a phenotypic variant of NUN 01009, said method comprises the steps of:
a) Providing a plurality of seeds of NUN 01009,
b) Optionally treating said seeds with a mutagenic agent,
c) Allowing the seeds to germinate and grow,
d) Identifying and/or selecting a phenotypic variant of NUN 01009, and
e) Optionally reproducing the phenotypic variant of NUN 01009.

In vitro propagation of triploid hybrid watermelons can be carried as described in Shalaby et al. 2008, Acta Biologica Szegediensis, Volume 52(1):27-31.

A further aspect of the invention relates to a method of producing transgenic plant of a plant designated NUN 01009 or of a phenotypic variant of NUN 01009, wherein said transgenic plant has at least distinguishing physiological and morphological characteristics 1) to 5) (described elsewhere herein), and optionally one or more of the distinguishing characteristics 6) to 12), when grown under the same environmental conditions of the variety designated NUN 01009 or the phenotypic variant of NUN 01009 and further comprises a desired trait, said method comprising transforming a NUN 01009 plant or cells or tissue of NUN 01009 (or of a phenotypic variant of NUN 01009 or cells or tissue thereof) with at least one transgene that confers said desired trait and regenerating a transgenic plant of NUN 01009 or of the phenotypic variant of NUN 01009 further comprising the transgene in its genome and comprising an additional trait conferred by said transgene.

All patent and non-patent literatures cited herein are incorporated by reference in their entireties.

GENERAL DEFINITIONS

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc Similarly, "a fruit" or "a plant" also refers to a plurality of fruits and plants.

As used herein, the term "plant" includes the whole plant or any parts or derivatives thereof, preferably having the same genetic makeup as the plant from which it is obtained. Plant parts or derivatives include plant organs (e.g. harvested or non-harvested fruits, leaves, flowers, anthers, etc.), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants, such as plant cuttings, embryos, pollen, anthers, ovules, fruits (e.g. harvested tissues or organs), flowers, leaves, seeds, clonally propagated plants, roots, stems, root tips, grafts (scions and/or root stocks) and the like. Also any developmental stage is included, such as seedlings, cuttings prior or after rooting, etc. Thus, when referring to NUN 01009 plants herein, it is understood that also grafts comprising scions of NUN 01009 plants are encompassed.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found.

"Diploid plant" refers to a plant, vegetative plant part(s), or seed from which a diploid plant can be grown, having two sets of chromosome, designated herein as 2n.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of triploid plants, by producing an appropriate amount of pollen at the appropriate day-time and for an appropriate period of time.

"Male parent" refers to the pollenizer plant used as male parent for inducing fruit set and seed production on a tetraploid female parent, resulting in F1 hybrid triploid seeds, such as seeds designated NUN 01009. Optionally one or both the male parent and the female parent are inbred. If both the male and female parent are inbred, i.e. each parent is nearly homozygous and stable the resulting hybrid triploid will also be genetically uniform and stable, like NUN 01009.

"Female parent" or "tetraploid parent" refers to the plant which is pollinated with pollen of the male parent, leading to the production of fruits containing triploid seeds, such as seeds designated NUN 01009. The female parent optionally is inbred so that it is nearly homozygous and stable.

"Hybrid triploid plant" or "F1 triploid" is a triploid plant grown from hybrid, triploid seed obtained from cross fertilizing a male diploid parent with a female tetraploid parent.

"Seedless fruit" are triploid fruit which contain no mature seeds. The fruit may contain one or more small, edible, white ovules.

"Grafting" refers to the method of joining of (genetically) different plant parts, especially scions and rootstocks, together so that they grow as a single plant. A grafted seedling or a grafted plant is a seedling or plant (produced by grafting) consisting of such different plant parts and which grows as one plant.

A "non-grafted" watermelon seedling or plant refers to a seedling or plant grown from a seed (without grafting).

A "single grafted" watermelon seedling or "single grafted" watermelon plant refers to a grafted seedling or plant consisting of a single watermelon scion (e.g. a triploid watermelon scion or a diploid watermelon scion) joined with a genetically different rootstock such as a gourd or squash rootstock, another watermelon rootstock, a transgenic rootstock, etc.

A "double grafted" watermelon seedling or a "double grafted" watermelon plant is herein a grafted seedling or plant comprising two watermelon scions grafted onto a single rootstock. In one aspect two genetically different watermelon scions, namely a triploid watermelon scion and a diploid watermelon scion, are grafted onto a genetically different rootstock, such as a gourd or squash rootstock, another watermelon rootstock, a transgenic rootstock, etc. In another aspect two triploid watermelon scions, or two diploid watermelon scions, are grafted onto a genetically different rootstock, such as a gourd or squash rootstock, another watermelon rootstock, a transgenic rootstock, etc.

A "scion" or "watermelon scion" refers to the part of a watermelon seedling that is grafted onto the rootstock and that develops into the aerial part of the plant.

"Rootstock" or "watermelon compatible rootstock" refers to the root system and stem onto which the watermelon scions are grafted and which provides the root system for the grafted seedling and grafted plant. It is noted that during the grafting process, the rootstock root system may be removed, which later grows back to develop a functional root system of the grafted seedling. Thus, when referring to the rootstock during the grafting method, this rootstock may be with or without the root system. When referring to the rootstock of the grafted seedlings or plants, the re-grown root system is encompassed.

A "transplant" or "seedling transplant" refers to a watermelon seedling which is at a developmental stage and condition so that can be transplanted into the field or greenhouse for growth, fruit production and harvest. The word transplant or seedling transplant can thus encompass single-grafted, double grafted or non-grafted seedlings.

"Interplanting" refers to the combination of two or more types of seeds and/or transplants sown or planted (or transplanted) on the same field, especially the sowing and/or planting (or transplanting) of pollenizers in the same field as triploid hybrid plants (for seedless fruit production on the triploid plants and diploid fruit production on the pollenizer plants). For example, the pollenizer may either be planted in separate rows or interplanted with the triploid plants in the same row (e.g. in hills within each row). Pollenizers may also be planted in between rows of triploids. Also seeds of pollenizers and triploid hybrids may be mixed prior to seeding, resulting in random seeding. The transplants of the triploid hybrid plants and/or pollenizer plants may also comprise a rootstock of a different plant. Suitable rootstocks are known in the art. Watermelon plants with a different rootstock are referred to as "grafted".

"Planting" or "planted" refers to seeding (direct sowing) or transplanting seedlings (plantlets) into a field by machine or hand.

"Vegetative propagation", "vegetative reproduction" or "clonal propagation" or are used interchangeably herein and refers to propagation of plants from vegetative tissue, e.g. by in vitro propagation or grafting methods (using scions). In vitro propagation involves in vitro cell culture or tissue culture (the cells or tissue are also referred to as explants) and regeneration of a whole plant from the in vitro culture. Grafting involves propagation an original plant by grafting onto rootstock. Clones (i.e. genetically identical vegetative propagations) of the original plant can, thus, generated by either in vitro culture or grafting.

"Regeneration" refers to the development of a plant from cell culture or tissue culture or vegetative propagation or from grafting, i.e. from a scion grafted onto a root-stock.

Throughout this document "average" and "mean" are used interchangeably and refer to the arithmetic mean. Thus, the term "mean" or "average" refers to the arithmetic mean of several measurements. The skilled person understands that the appearance of a plant depends to some extent on the growing conditions of said plant. Thus, the skilled person will know typical growing conditions for watermelons of the types described herein. The mean, if not indicated otherwise within this application, refers to the arithmetic mean of measurements on at least 5, preferably at least 10, more preferably at least 15 different, randomly selected plants or plant parts of a variety at a required developing stage.

"Yield" means the total weight of all watermelon fruits harvested per hectare of a particular line or variety.

"Marketable yield" means the total weight of all marketable watermelon fruits, especially seedless triploid fruit of at least 2.5 kg, harvested per hectare of a particular line or variety, i.e. fruits suitable for being sold for fresh consumption, having good flavor (no off-flavors), at least 10% brix (or Total Soluble Solids, TSS, as determined using a refractometer) and flesh color properties and no or very low levels of deficiencies such as hollow heart.

"Hollow heart" is a disorder that varies among varieties. Hollow heart is marked by cracks in the heart of the watermelon fruit owing to accelerated growth in response to ideal growth conditions facilitated by ample water and warm temperatures.

The terms "NUN 01009 WMW", "watermelon plant designated NUN 01009", "NUN 01009", or "variety designated NUN 01009" refer to a watermelon plant/variety of watermelon, representative seed of which having been deposited under Accession Number NCIMB 42569.

"USDA descriptors" are the plant variety descriptors described for watermelon in the "Objective description of Variety Watermelon (*Citrullus lanatus* (Thunb.) Matsum. & Nakai", ST-470-18 (dated Jul. 1, 2009) as published by U.S. Department of Agriculture, Agricultural Marketing Service, Science and Technology, Plant Variety Protection Office, Beltsville, Md. 20705 (available on the world wide web at ams.usda.gov/AMSv1.0/) and which can be downloaded from the world wide web at ams.usda.gov/AMSv1.0/ams.fetchTemplateData.do?template=TemplateJ&page=PVPOF orms.

"UPOV descriptors" are the plant variety descriptors described for watermelon in the "Guidelines for the Conduct of Tests for Distinctness, Uniformity and Stability," TG/142/4 (dated 2004-03-31, as published by UPOV (International Union for the Protection of New Varieties and Plants, available on the world wide web at upov.int) upov.int/en/publications/tg_rom/tg_index.html. Likewise, "UPOV methods" to determine specific parameters for the characterization of watermelon are described at upov.int.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Groben 8.D-97877 Wertheim, Article-No.: Art62-00008 EAN-Nr.: 4250193402112).

A plant having "essentially all the physiological and morphological characteristics" of NUN 01009 means a plant having the physiological and/or morphological characteristics when grown under the same environmental conditions of NUN 01009 as listed in Table 1. A plant having "essentially all the physiological and morphological characteristics of NUN 01009, except one, two, three, four or five characteristics" means that the watermelon plant, when grown under the same environmental conditions, (statistically) significantly differs from NUN 01009 in 1, 2, 3, 4 or 5 characteristics listed in Table 1, but does not differ significantly in the other morphological and/or physiological characteristics of NUN 01009 listed in Table 1.

"Distinguishing characteristics" or "distinguishing morphological and/or physiological characteristics" refers herein to the characteristics which are distinguishing between NUN 01009 and other triploid watermelon varieties, such as Millionaire, when grown under the same environmental conditions, especially the following characteristics: 1) the stem diameter at the second node; 2) the average mature fruit length; 3) the average mature fruit diameter at mid-section; 4) the average mature fruit weight and 5) the rind thickness at mid-section of the fruits. In one aspect the distinguishing characteristics further include at least one, two, three or more (or all) of the following characteristics: 6) the number of staminate and pistillate flowers; 7) the ratio vine length (cm): No. of internodes (at last harvest); 8) the size of staminate and pistillate flowers; 9) the flower color; 10) the primary fruit color; 11) the flesh color at maturity, and 12) the percentage of fruits developing Hollow heart. Thus, a watermelon plant "comprising the distinguishing characteristics of NUN 01009", refers herein to a watermelon plant which does not differ significantly from NUN 01009 in characteristics 1) to 5) above. In a further aspect the watermelon plant further does not differ significantly from NUN 01009 in at least one, two, three, four, five or all six characteristics selected from characteristics 6) to 12) above (also referred to as "further distinguishing characteristics").

The terms "phenotypic variant of NUN 01009 WMW", "phenotypic variant of watermelon plant designated NUN 01009", "variant of NUN 01009" refer to a watermelon plant/variety of watermelon (statistically significantly) differs from NUN 01009 in one, two or three or more physiological and/or morphological characteristics when grown under the same conditions, but which comprises the distinguishing characteristics 1) to 5) above (and optionally also one or more of 6) to 12) above) of NUN 01009 WMW when grown under the same conditions. In one aspect the variant of NUN 01009 WMW is derived from cells or tissues of NUN 01009, representative seed of which having been deposited under Accession Number NCIMB 42569.

An "Essentially Derived Variety" (EDV) shall be deemed to be essentially derived from another variety, "the initial variety", under the following circumstances: (i) it is predominantly derived from the initial variety, or from a variety that is itself predominantly derived from the initial variety, while retaining the expression of the distinguishing characteristics and optionally of one or more further distinguishing characteristics, and optionally of essentially all characteristics, that result from the genotype or combination of genotypes of the initial variety; and (ii) it is clearly distinguishable from the initial variety (e.g., one, one or more, two, two or more, three, three or more characteristics are different from the initial variety); and (iii) except for the differences which result from the act of derivation, it conforms to the initial variety in the expression of the distinguishing characteristics and optionally of one or more further distinguishing characteristics, and optionally of the essential characteristics that result from the genotype or combination of genotypes of the initial variety.

Thus, an EDV may be obtained for example by the selection of a natural or induced mutant, or of a somaclonal variant, or an off-type, the selection of a variant individual from plants of the initial variety, or transformation by genetic engineering. Such a variant may be selected at any time, e.g. in the field or greenhouse, during breeding, during or after in vitro culture of cells or tissues, during regeneration of plants, etc. The term EDV, thus, also encompassed a "phenotypic variant" derived from NUN 01009 seed, plant tissue or cells.

"Crossing" refers to the mating of two parent plants. Equally "Cross-pollination" refers to fertilization by the union of two gametes from different plants.

"Transgene" or "chimeric gene" refers to a genetic locus comprising a DNA sequence which has been introduced into the genome of a watermelon plant by transformation. A plant comprising a transgene stably integrated into its genome is referred to as "transgenic plant".

"Substantially equivalent" or "not significantly different" refers to a characteristic that, when compared, does not show a statistically significant difference (e.g., p≥0.05 using ANOVA) from the mean. Vice versa, "significantly different" or "statistically significantly different" refers to a characteristic that, when compared, does show a statistically significant difference (e.g., p<0.05 using ANOVA) from the mean.

DETAILED DESCRIPTION

The present invention provides a new type of watermelon (Citrullus lanatus) variety, designated NUN 01009. Watermelon variety designated NUN 1009 is a triploid variety which produces "icebox" sized fruit, which are seedless.

Variety NUN 01009 is most similar to the commercially available variety Millionaire (Harris Moran). However, NUN 01009 differs from Millionaire in one or more, e.g., at least two, at least three, optionally all morphological and/or physiological characteristics listed in the following (herein referred to as distinguishing characteristics; see also Table 1), when grown under the same environmental conditions:

1) the stem diameter at the second node is significantly smaller in NUN01009 compared to Millionaire (USDA criterion 6. STEM); thus, in one aspect, the average stem diameter at the second node of plants of the invention is at least about 0.5 mm, 1.0 mm, 1.5 mm, 2.0 mm, or more, smaller than compared to the most similar variety Millionaire.

2) the average mature fruit length is significantly longer in NUN 01009 compared to Millionaire (USDA criterion 9. MATURE FRUIT); thus, in one aspect, the average mature fruit length of plants of the invention is at least about 0.5 cm, 1.0 cm, 1.5 cm, 2 cm, 2.5 cm, 3 cm, or more, longer than that of the most similar variety Millionaire.

3) the average mature fruit diameter at mid-section is significantly larger in NUN 01009 compared to Millionaire (USDA criterion 9. MATURE FRUIT); thus, in one aspect, the average mature fruit diameter at midsection of plants of the invention is at least about 0.5 cm, 1.0 cm, 1.5 cm, 2 cm, 2.5 cm, 3 cm, or more, larger than that of the most similar variety Millionaire.

4) the average mature fruit weight is significantly higher for NUN 01009 compared to Millionaire (USDA criterion 9. MATURE FRUIT); thus, in one aspect, the average mature fruit weight of plants of the invention is at least about 0.5 kg, 0.6 kg, 0.7 kg, 0.8 kg, 0.9 kg, 1.0 kg, or more, heavier than that of the most similar variety Millionaire.

5) the rind thickness of NUN 01009 at mid-section of the fruits is significantly less thick compared to Millionaire fruits (USDA criterion 10. RIND). thus, in one aspect, the average rind thickness at midsection of mature fruits of plants of the invention is at least about 0.5 mm, 1.0 mm, 1.5 mm, 2 mm, 2.5 mm, or more, thicker than that of the most similar variety Millionaire.

Other morphological and/or physiological differences between NUN 01009 and Millionaire (referred herein to as further distinguishing characteristics), in one, two, three or all of which NUN 01009 differs from Millionaire when grown under the same environmental conditions, are:

6) there are on average fewer staminate flowers and more pistillate flowers (at first fruit set) on NUN 01009 compared to Millionaire (USDA criterion 5. PLANT); thus, in one aspect, the average number of staminate flowers at first fruit set of plants of the invention is lower by at least about 0.4, 0.5, 0.6, 0.7, 0.8, 0.9, 1.0, or more, flowers compared to the most similar variety Millionaire and the average number of pistillate flowers at first fruit set of plants of the invention is higher by at least about 0.4, 0.5, 0.6, 0.7, 0.8, 0.9, 1.0, or more, flowers compared to the most similar variety Millionaire.

7) the ratio vine length (cm): No. of internodes (at last harvest) is lower in NUN 01009 compared to Millionaire plants (USDA criterion 6. STEM); thus, in one aspect the ratio vine length (cm): No. of internodes at last harvest of plants of the invention is lower by at least a value of 0.4, 0.5, 0.6, 0.7, 0.8, 0.9, 1.0 or more, compared to the most similar variety Millionaire. 8) the staminate and pistillate flowers are on average larger (have a significantly larger diameter across) in NUN 01009 compared to Millionaire (USDA criterion 8. FLOWER); thus, in one aspect, the average flower diameter across the staminate and/or pistillate flowers of plants of the invention is at least about 0.1 cm, 0.2 cm, 0.3 cm, 0.4 cm, 0.5 cm, 0.6 cm, 0.7 cm, 0.8 cm, or more, larger than that of the most similar variety Millionaire.

9) the flower color of NUN 01009 is different (have a different shade of yellow) than the flower color of the most similar variety Millionaire; in one aspect the flowers of plants of the invention have a different yellow color than RHS Yellow Group 3D; e.g. they have an RHS value of Yellow Group 10B, while Millionaire flowers have an RHS value of Yellow Group 3D (USDA criterion 8. FLOWER);

10) the primary fruit color of NUN 01009 is slightly darker than that of Millionaire; In one aspect, plants of the invention thus have a darker yellow green color than RHS 146B, e.g. they have an RHS value of Yellow Green 146A, compared to Yellow Green 146B in Millionaire (USDA criterion 9. MATURE FRUIT);

11) also the flesh color of NUN 01009 is slightly darker than that of Millionaire. In one aspect plants of the invention have a flesh color which is darker than RHS Red Group 44D, e.g. they havean RHS value Red Group 44B, while Millionaire has a value of RHS Red Group 44D (USDA criterion 11. FLESH);

12) further, significantly fewer fruits of NUN 01009 have Hollow heart (USDA criterion 11. FLESH). thus, in one aspect, the percentage of fruits of plants of the invention having Hollow heart is at least about 5%, 10%, 20%, 30%, 40%, 50%, 60%, 70%, 80%, 90%, 95%, or more, lower than for the most similar variety Millionaire.

The morphological and/or physiological differences between NUN 01009 and other known varieties, such as Millionaire can easily be established by growing NUN 01009 next to the other varieties (in the same field or greenhouse under the same environmental conditions), preferably in several locations which are suitable for triploid watermelon cultivation, and measuring morphological and/or physiological characteristics of a number of plants (e.g., to calculate an average value (of at least 5, preferably at least 10, or even more, plants and/or plant parts which were grown under the same conditions) and to determine the variation/range/uniformity within the variety). Differences between varieties can be determined throughout the growing period as long as the plants to be compared develop the parts of said plants which are compared with each other.

For example, trials can be carried out in southern Europe, e.g. Spain, or the USA whereby e.g., growth (maturity) characteristics, plant characteristics (e.g. cotyledons, number of main stems at crown, number of flowers at first fruit set), main vine or stem characteristics (e.g. stem shape, diameter, stem surface, vine length, number of internodes), leaf characteristics (e.g. shape, presence or absence of lobes, leaf length, leaf width, leaf colors), flower characteristics (e.g. centimeters across, color), fruit characteristics at maturity (e.g. length, width, weight, rind/fruit surface, skin color, skin pattern, etc.), fruit rind characteristics (thickness, texture), fruit flesh characteristics at maturity (e.g. texture, coarseness, color, % TSS), regional and/or seasonal adaptation, pest and/or disease resistance/susceptibility can be measured and directly compared.

The morphological and/or physiological characteristics may vary with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the RHS-Chart (see, e.g., worldwide web: rhs.org.uk/Plants/RHS-Publications/RHS-colour-charts).

In one embodiment a watermelon plant is provided, designated NUN 01009, representative seeds of said triploid watermelon hybrid having been deposited under accession number NCIMB 42569.

In another aspect, a triploid watermelon plant is provided, which (statistically significantly) differs from NUN 01009 in at least one morphological and/or physiological characteristics, but which does not differ from NUN 01009 in the following characteristics when grown under the same conditions: 1) the stem diameter at the second node; 2) the average mature fruit length; 3) the average mature fruit diameter at mid-section; 4) the average mature fruit weight; and 5) the rind thickness at mid-section of the fruits.

In a further aspect, a triploid watermelon plant is provided, which (statistically significantly) differs from NUN 01009 in at least one morphological and/or physiological characteristics, but which does not differ from NUN 01009 in the following characteristics when grown under the same conditions: 1) the stem diameter at the second node; 2) the average mature fruit length; 3) the average mature fruit diameter at mid-section; 4) the average mature fruit weight; and 5) the rind thickness at mid-section of the fruits, and which further does not significantly differ from the plant designated NUN01009 in one or more of the following characteristics when grown under the same conditions: 6) the number of staminate and pistillate flowers at first fruit set; 7) the ratio vine length (cm): No. of internodes (at last harvest); 8) the size of staminate and pistillate flowers; 9) the flower color; 10) the primary fruit color; 11) the flesh color at maturity, and 12) the percentage of fruits developing Hollow heart.

In one embodiment any of the above triploid watermelon plants have 1) an average stem diameter at the second node of less than 12 mm, preferably less than 11 mm, e.g. between about 10 and 12 mm, e.g. between 10 and 11 mm; 2) an average mature fruit length of above 22 cm, e.g. above 23 cm, e.g. about 24 cm or about 23, 24 or 25 cm; 3) an average mature fruit diameter at mid-section of above 18 cm, above 19 cm, e.g. about 19 cm, 20 cm or 21 cm; 4) an average mature fruit weight of at least about 5.5 kg, or at least about 6 kg or at least about 6.1, 6.2, 6.3, 6.4 or 6.5 kg; and 5) an average rind thickness of the fruits at mid-section of less than 15 mm, e.g. less than or about 14 mm, or about 13 mm or about 13.5 mm, or between 13 and 15 mm, such as between 13.5 and 14.5 mm, and optionally one or more of the following characteristics: 6) the average number of staminate flowers at first fruit set is less than 7, preferably about 6, or 6.5 or 6.6, or 6.7 or 6.8 or 6.9; the average number of pistillate flowers at first fruit set is more than 2.8, preferably more than 3.0, e.g. about 3.0, 3.1, 3.2, 3.3, 3.4, 3.5; 7) the ratio vine length (cm): No. of internodes is less than 10.0, preferably less than 9.5, e.g. about 9.4, 9.3, 9.2, 9.1 or 9.0 or 8.9, or less; 8) the average diameter of staminate flowers is above 3.5 cm, preferably above 3.6, 3.7 cm, preferably about 3.8 cm, 3.9 cm or 4.0 cm and the average diameter of pistillate flowers is above 3.0 cm, preferably above 3.1, 3.2, 3.3, 3.4 or 3.5 cm, e.g. about 3.5, 3.6, 3.7, 3.8 or 3.9 or 4.0 cm; 9) the flower color has an RHS value of Yellow Group 10B; 10) the primary fruit color has an RHS value of Yellow Green 146A; 11) the flesh color at maturity has an RHS value of Red Group 44B, and 12) the percentage of fruits developing Hollow heart is less than 15%, preferably less than 10%, less than 5%, more preferably less than 2.5%, e.g. at most about 2% or 1%.

In a further embodiment a triploid watermelon plant is provided, which (statistically significantly) differs from the triploid watermelon plant designated NUN 01009, representative seeds of said triploid watermelon hybrid having been deposited under accession number NCIMB 42569, in at least 1, 2, 3, 4, or 5 morphological and/or physiological characteristics when grown under the same environmental conditions, whereby the morphological and/or physiological characteristics are those of Table 1. The triploid hybrid plant does, thus, not differ in a statistically significant way from NUN 01009 in any of the other morphological and/or physiological characteristics of Table 1 when grown under the same conditions.

In one embodiment a triploid watermelon plant is provided, designated NUN 01009, which does not (statistically significantly) differ in any of the morphological and/or physiological characteristics of Table 1 from plants grown from seeds deposited under accession number NCIMB42569 when grown under the same environmental conditions.

In one aspect, the above described triploid watermelon plants are obtained from in vitro cell or tissue cultures. As already mentioned, in vitro cell or tissue cultures are known in the art and can be used to either vegetatively reproduce the plant from which the cells or tissues were obtained or to identify and/or select phenotypic variants, and to regenerate such variants. Once selected, such selected variants can then in turn also be reproduced true to type using in vitro cell or tissue culture.

Thus, in one aspect, a triploid watermelon plant is provided which is clonally propagated (it is a vegetative reproduction) from NUN 01009 cells or tissue and which comprises all the distinguishing characteristics of NUN 01009 when grown under the same environmental conditions. In another aspect it further comprises one or more of the further distinguishing characteristics. In yet another aspect it comprises all morphological and/or physiological characteristics of NUN 01009 as given in Table. And in yet a further aspect it comprises all morphological and/or physiological characteristics of NUN 01009 as given in Table, except that it significantly differs from NUN 01009 in 1, 2, 3, 4, or 5 of the morphological and/or physiological characteristics of Table 1.

Also plant parts of the above triploid watermelon plants are provided. In one aspect the plant parts are selected from the group consisting of: explants, cells, protoplasts, callus, tissues, shoots, stems, meristem, leaf, scion, rootstock, root, cotyledon, hypocotyls, flower, fruit (especially seedless fruits produced after pollination with a diploid pollinizer).

Further, fruits produced on NUN 01009, or on a phenotypic variant of NUN 01009, after pollination of the flowers of NUN 01009, or of the flowers of the phenotypic variant of NUN 01009, are provided herein. The fruits are distinguished from other fruits by the fact that the average fruit characteristics of the distinguishing characteristics 2) to 5) (above) do not significantly differ from the fruit characteristics 2) to 5) of NUN 01009, a representative number of seeds having been deposited under Accession number NCIMB 42569, when grown under the same conditions.

Plants and plant parts and fruits of NUN 01009 are, in one aspect, obtainable by growing seeds of which a representative sample has been deposited under the Budapest Treaty with Accession Number NCIMB 42569 . Plants and plant parts and fruits of a phenotypic variant of NUN 01009 are, in one aspect, obtainable by in vitro cell- or tissue-culture of cells or tissues of NUN 01009 and selection/and or identification of a phenotypic variant (optionally after mutagenesis treatment) as described above.

Seeds

Also provided are seeds of watermelon variety NUN 01009. A representative sample of said seeds (at least 2500 seeds) has been deposited under the Budapest Treaty with Accession Number NCIMB 42569.

In one embodiment, a plurality of NUN 01009 seeds are packaged into small and/or large containers (e.g., bags, cartons, cans, etc.). Seeds may be treated with one or more chemical compounds and/or biological control agents (e.g. to improved germination, insecticidal-, acaricidal-, nematicidal- or fungicidal-compounds or compositions, etc.) and/or seeds may be primed. Biological control agents are one or more microorganisms which protect the seed or seedling against pathogens. For example, strains of bacteria and/or fungi, such as bacteria of the species of Streptomyces, Pseudomonas, Bacillus and Enterobacter or fungi of the species Phomopsis, Ectomycorrhizae, Trichoderma, Cladosporium and Gliocladium.

Priming is a water-based process that is performed on seeds to increase uniformity of germination and emergence from the soil, and thus enhance vegetable stand establishment. Methods how to prime triploid watermelon seeds are well known in the art, see WO2008/107097, describing different priming methods, such as hydro-priming (including drum-priming), osmopriming and solid-matrix priming, which can be used. The priming process may also be combined with the chemical compounds or compositions and/or biological control agent treatment, so seeds may e.g. be hydrated in a first step, dried in a second step and treated in a third step with one or more seed treatment compounds or compositions. Priming is also sometimes referred to as seed conditioning.

Hydropriming includes those techniques in which seeds are allowed to take up water for a short period or at low temperatures, mostly at ample water supply. These techniques are sometimes also referred to as soaking or steeping. Hydropriming of triploid watermelon seeds is for example described in Huang et al. 2002 (Kasetsart J. 36: 219-224).

With osmopriming, the seeds are exposed to an osmotic solution (see e.g. WO2008/107097).

With solid matrix priming (SMP), seeds are mixed with water and solid carriers. Examples of solid carriers are vermiculite and diatomaceous silica products. The water is taken up by the seeds as well as absorbed on the solid particle surfaces, which in this way control the water uptake of the seeds. In addition to using particle-like carriers, SMP can be carried out using, amongst others, moist towels, gunny bags, moist sand, sterilised compost or press mud as well.

So, in one aspect seeds of NUN 01009 are provided wherein said seeds are primed seeds and/or chemically and/or biologically treated seeds, comprising one or more chemical compounds or compositions and/or one or more biological control agents, selected from the group consisting of: a compound that improves germination, an insecticidal compound, an acaricidal compound, a nematicidal compound, and a fungicidal compound.

Plant and Parts of NUN 01009 or of a Phenotypic Variant of NUN 01009

The present invention provides plants, including seedlings, and plant parts designated NUN 01009.

In particular, the invention provides plants and plant parts, including seedlings, scions, and/or rootstocks of NUN 01009 obtained from germinating and growing the seeds of NUN 01009, a representative sample of seeds having been deposited under Accession number NCIMB 42569.

Other plant parts obtained from germinating NUN 01009 are triploid (3n) parts such as cuttings, cotyledons, stems, vines, leaves, flowers, roots, rootstocks, scions, or parts of any of these.

Also parts of the seed of NUN 01009 itself are provided herein, such as seed coat, embryo, or endosperm.

Thus, any developmental stage and any part of the plant grown from seeds of NUN 01009, or any part of the seed of NUN 01009, are provided herein.

Also, any plant regenerated from said plant part, i.e. any vegetative or clonal propagation of NUN 01009 is encompassed herein. This includes watermelon seedlings or plants grown from a scion and/or a rootstock of NUN 01009. It also includes plants of NUN 01009 grown from in vitro cell cultures or tissue cultures of cells or tissues of NUN 01009.

Thus, vegetative propagations of NUN 01009 may be generated by germinating seeds of NUN 01009 and obtaining plant cells or tissues from the seedling or from the plants grown from said seeds, or by obtaining cells or tissues from the seeds of NUN 01009, and regenerating a plant from said cells or tissue.

Alternatively, vegetative propagations of NUN 01009 may be generated by germinating the seeds of NUN 01009 and obtaining a scion from the seedling and grafting the scion to a suitable rootstock. The scion will develop into a plant having at least the distinguishing characteristics of NUN 01009, optionally also one or more further distinguishing characteristics of NUN 01009. In another aspect the vegetative propagation comprises all the physiological and/or morphological characteristics of NUN 01009 provided in Table 1, when grown under the same environmental conditions. In yet another aspect the vegetative propagation comprises all the physiological and/or morphological characteristics of NUN 01009 provided in Table 1, except for 1, 2, 3, 4, or 5 of those characteristics, when grown under the same environmental conditions.

Also provided are parts of the watermelon plants designated NUN 01009 such as cuttings, fruits or fruit parts, flowers, leaves, cotyledons, stems, roots, clonally propagated plants, root tips, grafts (scions and/or root stocks), seedlings, seeds, parts of the seed (seed coat, embryo, endosperm, embryo sac), flowers, stalks, hypocotyl, shoots, cells, protoplasts, meristems, buds etc. of variety NUN 01009, or parts of any of these. Such parts may vegetative cells or tissues, which include, without limitation cuttings, roots, stems, cells or protoplasts, leaves, cotyledons, meristems and buds.

Moreover, there is provided a cell culture or tissue culture of watermelon variety NUN 01009 in which the cell- or tissue culture is derived (or obtained) from a tissue such as, for example and without limitation, leaves, embryos, cotyledon, hypocotyls, meristematic cells, roots, root tips, flowers, seeds or stems. For example, leaf-, hypocotyl- or stem-cuttings may be used in tissue culture.

Also provided are watermelon plants regenerated from the above-described plant parts, or regenerated from the above-described cell or tissue cultures, said regenerated plant having at least the distinguishing characteristics of NUN 01009 when grown under the same conditions, optionally also one or more further distinguishing characteristics of NUN 01009. In another aspect the plants have all morphological and/or physiological characteristics of NUN 01009 measured in Table 1, or all except 1,2,3,4 or 5 of the characteristics measured for NUN 01009 in Table 1. These plants can also be referred to as "vegetative propagations of NUN 01009" or vegetative propagations of phenotypic variants of NUN 01009.

Also provided are harvested fruits of NUN 01009 or of a vegetative propagation of NUN 01009 or of a phenotypic variant of NUN 01009 and packages comprising a plurality of such fruits, especially mature, marketable fruits.

As already mentioned, also phenotypic variants of NUN 01009 are encompassed herein. In one embodiment, NUN 01009 seeds or cells or tissues of NUN 01009 may be mutated (by e.g. irradiation, chemical mutagenesis, heat treatment, etc.) and mutated seeds or or cells or plant parts or plants may be selected in order to change one or more characteristics of NUN 01009.

Also, NUN 01009 or a phenotypic variant of NUN 01009 may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 01009 by transforming NUN 01009 or a phenotypic variant thereof with a transgene that confers the desired trait, wherein the transformed plant retains all the distinguishing characteristics, optionally also one or more or all further distinguishing characteristics of NUN 01009. In one embodiment the transformed plant retains essentially all the morphological and physiological characteristics of NUN 01009 or of the phenotypic variant of NUN 01009 and contains the desired trait. In one embodiment the transformed plant retains essentially all except 1, 2, 3, 4, or 5 of the morphological and physiological characteristics of NUN 01009 measured in Table 1, or of the phenotypic variant of NUN 01009, and contains the desired trait.

The invention also provides a method of producing plants of variety designated NUN 01009, or a part thereof, or a phenotypic variant of NUN 01009, or a part thereof, comprising vegetative propagation of a plant designated NUN 01009 or designated a phenotypic variant of NUN 01009. In one embodiment, said vegetative propagation comprises regenerating a whole plant from a part of variety designated NUN 01009 or designated a phenotypic variant of NUN 01009. In one embodiment, said part of a plant is a cutting, root, stem, cell, protoplast, leaf, meristem, bud, cell culture or a tissue culture.

The method for vegetative reproduction of NUN 01009 (or a phenotypic variant of NUN 01009) comprises the steps of:
 a) Providing an explant of NUN 01009 (or of a phenotypic variant of NUN 01009),
 b) Culturing said explant in an in vitro culture,
 c) Providing a shooting and optionally a rooting medium to said explants,
 d) Allowing the plants or shoots to grow.

Explants may be any plant parts of NUN 01009 (or of a phenotypic variant of NUN 01009) which is regenerable into a whole plant or into a shoot, such as parts of cotyledons, shoot tips, embryos, hypocotyls, leaves, stalk, cells, protoplasts, callus, meristems, etc.

If a shoot is regenerated, the shoot may be grafted onto a rootstocks to grow a grafted plant comprising a scion of NUN 01009 or of a phenotypic variant of NUN 01009.

If plants are regenerated they may be transferred to soil.

The regenerated plants or grafted plant may be grown e.g. in the field or greenhouse to produced fruits.

The regenerated plants or grafted plants have all the distinguishing characteristics of NUN 01009, optionally also 1, 2, 3, 4 or 5 or all further distinguishing characteristics. In another embodiment the regenerated plants have essentially all, or all except 1, 2, 3, 4 or 5, of the physiological and/or morphological characteristics of NUN 01009.

In another aspect the invention provides a method for identifying and/or selecting a phenotypic variant of NUN 01009, said method comprises the steps of:
 a) Providing an explant of NUN 01009,
 b) Culturing said explant in an in vitro culture,
 c) Providing a shooting and a rooting medium to said explants,
 d) Allowing rooted plants to grow,
 e) Identifying and/or selecting a phenotypic variant.

Explants may be any plant parts of NUN 01009 which is regenerable into a whole plant, such as parts of cotyledons, shoot tips, embryos, hypocotyls, leaves, stalk, cells, protoplasts, callus, meristems, etc.

Optionally, the explants may be treated with a mutagen, such as X-rays, UV-radiation, EMS or another chemical mutagen, to induce genotypic and phenotypic variation. As mentioned earlier, the phenotypic variant is preferably stable in the altered characteristics, i.e. the modified phenotypic characteristic(s) is/are also seen in the mature plant. The phenotypic variant may also be clonally propagated, to produce many plants of the phenotypic variant and to produce fruits on those plants.

In vitro propagation of triploid hybrid watermelons can be carried as described in Shalaby et al. 2008, Acta Biologica Szegediensis, Volume 52(1):27-31. Herein different media are described which can be suitably used as shooting/shoot elongation or rooting media, see e.g. Materials and Methods on page 28.

In another aspect the invention provides a method for identifying and/or selecting a phenotypic variant of NUN 01009, said method comprises the steps of:
 a) Providing a plurality of seeds of NUN 01009,
 b) Optionally treating said seeds with a mutagenic agent,
 c) Allowing the seeds to germinate and grow,
 d) Identifying and/or selecting a phenotypic variant of NUN 01009.

Also in this method the phenotypic variant is preferably stable in the altered characteristics, i.e. the modified phenotypic characteristic(s) is/are also seen in the mature plant. The phenotypic variant may also be clonally propagated, to produce many plants of the phenotypic variant and to produce fruits on those plants.

Thus, a vegetative propagated plant (or a part thereof) is provided having the distinguishing characteristics of NUN 01009; optionally having one or more of the further distinguishing characteristics of NUN 01009. In one embodiment the vegetative propagated plant has all the essential morphological and physiological characteristics of the watermelon plant designated NUN 01009 when grown under the same environmental conditions. In some embodiments, said propagated plant differs from NUN 01009 in 1, 2, 3, 4, or 5 of the characteristics of Table 1, but otherwise has all the essential and/or morphological characteristics of NUN 01009 when grown under the same conditions.

When referring to the morphological and/or physiological characteristics of Table 1, or as described or measured in Table 1, it is understood that the characteristics named under the heading USDA Descriptor.

The invention also provides for a method of producing a vegetatively propagated plant of variety designated NUN 01009, or a part thereof, comprising regeneration of said plant from a cell culture or a tissue culture. Also provided are plants which are regenerated from such a cell culture or tissue culture.

As described above, the invention also relates to a phenotypic variant of NU 01009 and a method for producing such as variant. The phenotypic variant differs from NUN 01009 in one or more or a few morphological and/or physiological characteristics, but is still genetically closely related to NUN 01009. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 01009 if its DNA fingerprint is at least 80%, 90%, 95%, 97% or 98% identical to the fingerprint of NUN 01009. In a preferred embodiment amplified fragment length polymorphism (AFLP) markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (van Eeuwijk and Law (2004), Euphytica 137: 129-137). In one embodiment a closely related plant of NUN 01009 has a Jaccard Similarity index of higher than 0.96.

Transgene

Also provided is a method of producing a watermelon plant having a desired trait, wherein the method comprises transforming the watermelon plant or plant part or cell of the invention with a transgene that confers the desired trait, wherein the transformed and regenerated plant retains the distinguishing characteristics of NUN 01009 and optionally also one or more or all further distinguishing characteristics of NUN 01009 and contains the desired trait; or which retains essentially all phenotypic and/or morphological characteristics of a NUN 01009 plant of the invention and contains the desired trait; or which retains essentially all phenotypic and/or morphological characteristics of a NUN 01009 plant of the invention except 1, 2, 3, 4, or 5, and contains the desired trait. Thus, a transgenic watermelon plant of NUN 01009 or of a phenotypic variant of NUN 01009 is provided which comprises a new trait due to the transgene in its genome. Also a transgenic rootstock and/or scion of such a plant is provided.

Many useful traits that can be introduced into NUN 01009 or into a phenotypic variant of NUN 01009, such as herbicide resistance, disease resistance (against fungi or viruses or bacteria), insect resistance, etc.

Methods for transforming watermelon are known in the art, see e.g. Li et al. 2012 African Journal of Biotechnology Vol. 11(24), pp. 6450-6456 describing Agrobacterium transformation of watermelon; or Park et al. 2005, Plant Cell Rep. 24(6):350-6, describing transgenic rootstock having virus resistance.

DNA sequences, whether from a different species or from the same species, which are inserted into the genome using transformation, are referred to herein collectively as "transgenes". A "transgene" also encompasses antisense, or sense and antisense sequences capable of gene silencing. Thus, the present invention also relates to transgenic NUN 01009 plants (or a transgenic phenotypic variant of NUN 01009) and plant parts (e.g. rootstock or scion). In some embodiments of the invention, a transgenic NUN 01009 plants (or a transgenic phenotypic variant of NUN 01009) or plant parts may contain at least one transgene but could contain at least 1, 2, 3, 4, 5, 6, or more transgenes.

Various genetic elements can be introduced into the plant genome using transformation. These elements include, but are not limited to genes, coding sequences, inducible-, constitutive-, and tissue specific promoters, enhancing sequences, and signal and targeting sequences.

Plant transformation involves the construction of an expression vector which will function in plant cells. Such a vector comprises DNA comprising a gene under control of, or operatively linked to, a regulatory element (for example a promoter). The expression vector may contain one or more such operably linked gene/regulatory element combinations. The vector(s) may be in the form of a plasmid and can be used alone or in combination with other plasmids to provide transformed watermelon plants using transformation methods as described below to incorporate transgenes into the genetic material of the watermelon plant(s).

Method for Interplanting

In one embodiment a method for producing triploid watermelon fruits in a field is provided, said method comprising:
(a) interplanting NUN 01009 plants according to the invention (or a phenotypic variant of NUN 01009 according to the invention) and diploid pollenizers in one field,
(b) allowing pollination of flowers of the triploid hybrid plants,
(c) optionally harvesting triploid fruits.

Step c) may comprise harvesting fruits produced on the pollenizer plants.

In step a) different planting schemes can be applied. Basically, in the traditional triploid production field, the triploid hybrids and pollenizer plants may be interplanted at regular intervals in the same row (e.g. 1, 2, 3 or 4 consecutive triploid plants followed by one pollenizer plant, etc.), or rows of triploid hybrids and pollenizer plants may alter at certain intervals (e.g. 1, 2, 3 or 4 rows of triploids followed by one row of pollenizer plants). Alternatively, the triploids are planted in rows and the pollenizer plants are planted at regular intervals in-between rows Thus, the same field arrangement as for traditional triploid watermelon production can be used.

Thus, a field may comprising triploid hybrid watermelon seedlings and the pollenizer seedling according to the invention in a ratio of 5:1, 4:1, 3:1, 2:1 or 1:1.

In one embodiment each of 5, 4, 3, 2 or 1 consecutive plants are triploid hybrid watermelon seedling according to the invention followed by at least one pollenizer seedling. Optionally each of the consecutive triploid hybrid plants according to the invention may also be followed by 2 or 3 pollenizer seedling.

In another embodiment the field comprises rows of only triploid hybrids and rows of only pollenizer seedlings, whereby the ratio of triploid rows to pollenizer rows is 5:1, 4:1, 3:1, 2:1, or optionally 1:1.

The hybrid triploids may be non-grafted or grafted plants. The pollinizer may be any diploid pollenizers, for example known pollenizers are Polimax F1 or Jenny F1 (Nunhems), Red Star F1 (Nunhems), Super-pollenizers SP-1, SP-2, SP-3, SP-4, SP-5 or SP-6 (Syngenta), Companion (Seminis), Escort-4 (Gold Seed Co. US 2009/0288183) or others. The pollenizer may produce marketable fruits (seeded) and may be an open pollinated or hybrid diploid. Alternatively, the pollenizer may produce non-marketable fruits. The pollenizer plant or seedling may also be grafted or non-grafted.

Optimal distances between plants and between rows may vary greatly depending on location, growing conditions, etc. Distances between plants may thus be any distance, such as about 3 feet (about 90 cm), about 4 feet (about 120 cm), about 5 feet (about 150 cm) or about 6 feet (about 180 cm) or more.

In step b) pollination is allowed to occur, whereby the female flowers of the triploid hybrid plants are pollinated with pollen of the diploid pollenizer plants. Pollination of triploid flowers results in seedless, triploid fruits, which can then be harvested in step c). Also pollination of the diploid flowers of the pollenizer plants will result in diploid, seeded fruits. Thus diploid fruits (which may also be marketable, depending on the pollenizer used) may be harvested from the also. If the diploid pollenizer produced non-marketable fruits, these can be harvested and discarded and/or left in the field. For example, pollenizers comprising the explosive-rind-gene produce non-marketable fruits, which may be left on the plants and/or in the field.

Pollination is usually done by bees, and bee hives can be provided to the fields unless sufficient wild bees are naturally present. Pollination can also be performed by manual or mechanical means. Harvest at maturity may be done by hand or mechanized.

Optionally harvested diploid and/or triploid fruit are placed into containers, preferably into different containers. Thus, in one embodiment a container comprising solely triploid fruits from triploid hybrids according to the invention. Any type of container may be used, e.g. cartons, boxes, etc.

Products

Also provided are plant parts derived from seeds of variety NUN 01009, or from a vegetatively propagated plant of NUN 01009 (or of a phenotypic variant of NUN 01009), being selected from the group consisting of: harvested (mature or immature) fruits or parts thereof, cotyledons, stems or parts thereof, roots or parts thereof, cuttings or parts thereof, rootstock, scion, flowers, florets, or flower buds, shoot, shoot tips, hypocotyls, embryo.

The invention also provides for a food or feed product comprising or consisting of a plant part described herein, especially a fruit or fruit part, of the plants described herein. The food or feed product may be fresh or processed, e.g., canned, steamed, boiled, fried, blanched and/or frozen etc.

For example, containers such as cans, boxes, crates, bags, cartons, Modified Atmosphere Packagings, films (e.g. biodegradable films), etc. comprising plant parts of plants, especially fruits parts (fresh and/or processed) designated NUN 01009 (or of a phenotypic variant of NUN 01009) are also provided herein.

Deposit Information

A total of 2500 seeds of the variety NUN 01009 are deposited by Nunhems B.V. on Apr. 18, 2016 at the NCIMB Ltd., Ferguson Building, Craibstone Estate, Bucksburn, Aberdeen AB219YA, United Kingdom (NCIMB). The deposit has been assigned Accession Number NCIMB 42569. A deposit of NUN 01009 and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in plant breeding, chemistry, biology or related fields are intended to be within the scope of the following claims.

The following non-limiting examples illustrate the invention.

EXAMPLES

Development of NUN 01009

The triploid hybrid variety NUN 01009 was developed from a cross between tetraploid female and diploid male parent line.

The seeds of NUN 01009 can be grown to produce plants and parts thereof. The variety NUN 01009 can be propagated by vegetative propagation.

NUN 01009 characteristics were compared with those of Millionaire (Harris Moran) according to standards of the U.S. Department of Agriculture, Agricultural Marketing Service, Science and Technology, Plant Variety Protection Office, Beltsville, Md. 20705. Trials were carried out by Nunhems USA Inc., in Acampo, Calif. (US) in 2012.

Characteristics of NUN 01009

Table 1 shows the USDA descriptors of NUN 01009 and Millionaire of a field trial in Acampo, Calif., US. At least 15 to 25 plants or plant parts were randomly selected from two replications of a field trial in Acampo, USA. These plants or plant parts were used to measure characteristics. The values are mean values. The 'distinguishing characteristic' and 'further distinguishing characteristics' are in bold. Table 1

TABLE 1

| Distinguishing characteristics 1)-5) and further distinguishing character. 6)-12) | USDA descriptor | NUN01009 | Millionaire |
|---|---|---|---|
| | 1. General Fruit Type | | |
| | 1 = Oblong, 2 = Round Large, 3 = Round small (icebox) | 3 | 3 |

TABLE 1-continued

| Distinguishing characteristics 1)-5) and further distinguishing character. 6)-12) | USDA descriptor | NUN01009 | Millionaire |
|---|---|---|---|
| | 2. Area of best adaptation | | |
| | 1 = Southern US, 2 = Northeast/Central US, 3 = Southwest US, 4 = Most US Areas | 4 | 4 |
| | 3. Maturity | | |
| | No. of days from emergence to anthesis | 50 | 49 |
| | No. of days from pollination to maturity | — | — |
| | Days Relative Maturity (as reported in seed catalogs) | 86 | 84 |
| | Maturity category 1 = early, 2 = medium, 3 = late | 2 | 2 |
| | 4. Ploidy | | |
| | 1 = diploid, 2 = tetraploid, 3 = triploid | 3 | 3 |
| | 5. PLANT | | |
| | Cotyledon shape 1 = flat, 2 = folded | 1 and 2 | 1 and 2 |
| | Plant sex form 1 = monoecious, 2 = andromonoecious | 1 | 1 |
| | No. of main stems at crown | 3 | 3 |
| 6) | Number of flowers per plant at first fruit set Staminate flowers | 6.6 | 7.2 |
| 6) | Number of flowers per plant at first fruit set Pistillate flowers | 3.4 | 2.6 |
| | 6. STEM | | |
| | Stem shape (cross section) 1 = round, 2 = angular | 2 | 2 |
| | Stem surface 1 = glabrous, 2 = scabrous, 3 = pubescent, 4 = bristled | 3 | 3 |
| 1) | Diameter (mm) at second node | 10.8 | 12.5 |
| | Vine length (cm) (at last harvest) | 334 | 357 |
| | No. of Internodes (at last harvest) | 36 | 34.8 |
| 7) | Ratio Vine length (cm): No of internodes (at last harvest) | 9.3 | 10.3 |
| | 7. LEAF | | |
| | Leaf shape 1 = ovate, 2 = obovate, 3 = round | 1 | 1 |
| | Leaf lobes 1 = none, 2 = lobed | 2 | 2 |
| | Leaf length (cm) | 12.7 | 12.6 |
| | Leaf width (cm) | 13.7 | 14.4 |
| | Leaf size 1 = longer than wide, 2 = length-width equal, 3 = wider than long | 1 | 1 |
| | Dorsal surface pubescence 1 = smooth, 2 = pubescent | 2 | 2 |
| | Ventral surface pubescence 1 = smooth, 2 = pubescent | 2 | 2 |
| | Leaf color 1 = light green, 2 = gray green, 3 = medium green, 4 = dark green | 3 | 3 |
| | Color chart name | RHS | RHS |
| | Color chart value | Yellow Green 147B | Yellow Green 147B |
| | 8. FLOWER | | |
| 8) | Diameter across Staminate (cm) | 3.8 | 3.5 |
| 8) | Diameter across Pistillate (cm) | 3.6 | 3.0 |
| | Flower color: 1 = lemon yellow, 2 = yellow, 3 = orange | 2 | 2 |
| | Color chart name | RHS | RHS |
| 9) | Color chart value | Yellow Group 10B | Yellow Group 3D |
| | 9. MATURE FRUIT | | |
| | Fruit shape 1 = round, 2 = oval, 3 = cylindrical | 2 | 2 |
| 2) | Long (cm) | 23.9 | 21.4 |

TABLE 1-continued

| Distinguishing characteristics 1)-5) and further distinguishing character. 6)-12) | USDA descriptor | NUN01009 | Millionaire |
|---|---|---|---|
| 3) | Diameter at midsection (cm) | 20.1 | 17.7 |
| 4) | Average weight (kg) | 6.1 | 5.3 |
|  | Maximum fruit weight (kg) | 7.42 | 6.66 |
|  | Index = length ÷ diameter × 10 | 11.9 | 12.1 |
|  | Fruit surface<br>1 = smooth, 2 = slightly grooved, 3 = deeply grooved | 1 | 1 |
|  | Skin color pattern<br>1 = solid (one color), 2 = stripe, 3 = mottle/net | 2 | 2 |
|  | Primary color<br>1 = Yellow Green (Desert King), 2 = Light Green (Charleston Gray), 3 = Medium Green (Sugar baby), 4 = dark green (Florida Giant) | 3 | 3 |
|  | Color chart name | RHS | RHS |
| 10) | Color chart value | Yellow Green 146A | Yellow Green 146B |
|  | Secondary color<br>1 = Yellow Green, 2 = Light Green, 3 = Medium green, 4 = dark green | 1 | 1 |
|  | Color chart name | RHS | RHS |
|  | Color chart value | Yellow Green 145D | Yellow Green 145D |
|  | 10. RIND |  |  |
|  | Rind texture<br>1 = tender, 2 = brittle, 3 = tough | 3 | 3 |
|  | Thickness blossom end (mm) | 17.1 | 17.4 |
| 5) | Thickness sides (mm) | 13.9 | 15.6 |
|  | 11. FLESH |  |  |
|  | Flesh texture<br>1 = crisp, 2 = soft | — | 2 |
|  | Flesh coarseness<br>1 = course fibrous, 2 = fine—little fiber | 2 | 2 |
|  | Flesh color<br>1 = white, 2 = yellow, 3 = orange, 4 = pink, 5 = red, 6 = dark red | 5 | 5 |
|  | Color chart name | RHS | RHS |
| 11) | Color chart value | Red Group 44B | Red Group 44D |
|  | Refractometer: % Soluble solids of juice (Center of fruit) | 12 | 11.9 |
| 12) | % Hollow heart | 1 | 20 |
|  | % placental separation | 0 | 0 |
|  | % traverse crack | 0 | 15 |

— = not measured;
NA = not applicable

These are typical values. Values may vary due to environment. Other values that are substantially equivalent are also within the scope of the invention.

NUN01009 further also has resistance against *Fusarium* wilt race 0.1 and against Sunburn.

The invention claimed is:

1. A triploid watermelon plant, designated NUN 01009, or part thereof, a representative sample of seeds of which having been deposited under Accession Number NCIMB 42569.

2. A seed designated NUN 01009, a representative sample of seeds having been deposited under Accession Number NCIMB 42569.

3. The triploid watermelon plant or part thereof of claim 1, produced by in vitro culture or grafting of a scion derived from NUN 01009 to a different rootstock.

4. A fruit produced on the plant of claim 1.

5. A plant cell culture or tissue culture of the watermelon plant or part thereof of claim 1 or of the seed or part of the seed of claim 2.

6. The plant part of claim 1, wherein the part is selected from the group consisting of: a scion, a rootstock, a cell, a cotyledon, a fruit, a shoot, a shoot tip, a root, a hypocotyl, an embryo, a protoplast, a leaf, a meristem, a flower or a stem, or a part of any of these.

7. A watermelon plant regenerated from the plant part of claim 1, wherein the part is selected from the group consisting of: a scion, a rootstock, a cell, a cotyledon, a fruit, a shoot, a shoot tip, a hypocotyl, an embryo, a seed, a protoplast, a leaf, a meristem, a flower or a stem, or a part of any of these, and wherein the regenerated plant comprises all of the morphological and physiological characteristics of NUN 01009 when grown under the same environmental conditions, a representative sample of seeds of NUN 01009 having been deposited under Accession Number NCIMB 42569.

8. A fruit produced on the plant of claim 7.

9. A method of producing seedless watermelon fruits, said method comprising:
   a) interplanting a plant of claim 1 or a plant of claim 7, with a pollinizer plant in one field:

b) allowing the pollen of the pollinizer to pollinate the flowers of the plant of claim 1 or 7, c) harvesting the fruit from the plants of claim 1 or 7; and optionally d) packaging the fruits into containers.

10. The seed of claim 2, wherein the seed is primed and/or wherein the seed further comprises one or more compounds or compositions selected from: a biological control agent, a fungicidal composition, a insecticidal composition, a nematicidal composition or an acaricidal composition.

11. The plant of claim 1, wherein the plant comprises a different rootstock.

12. The plant of claim 7, wherein the plant comprises a different rootstock.

\* \* \* \* \*